United States Patent [19]

Conder et al.

[11] Patent Number: 5,223,415

[45] Date of Patent: Jun. 29, 1993

[54] BIOSYNTHETIC PRODUCTION OF 7-[1',2',6',7',8',8A'(R)-HEXAHYDRO-2'(S),6'(R)-DIMETHYL-8'(S)-HYDROXY-1'(S)-NAPHTHYL]-3(R),5(R)-DIHYDROXYHEPTANOIC ACID (TRIOL ACID)

[75] Inventors: Michael J. Conder; Steven J. Cianciosi, both of Harrisonburg, Va.; William H. Cover, Lansdale, Pa.; Rebecca L. Dabora, Andover, Mass.; Eric T. Pisk; Robert W. Stieber, both of Harrisonburg, Va.; Bogdan Tehlewitz, McGaheysville; Gregory L. Tewalt, Shenandoah, both of Va.

[73] Assignee: Merck & Co., Inc., Rahway, N.J.

[21] Appl. No.: 832,545

[22] Filed: Feb. 7, 1992

Related U.S. Application Data

[63] Continuation-in-part of Ser. No. 788,691, Nov. 6, 1991, abandoned, which is a continuation of Ser. No. 597,643, Oct. 15, 1990, abandoned.

[51] Int. Cl.$^5$ .................. C12P 17/00; C12P 17/06; C12N 9/14; C07D 309/30
[52] U.S. Cl. .................. 435/125; 435/117; 435/41; 435/183; 435/195; 549/292
[58] Field of Search .......... 435/125, 117, 41, 183, 435/195; 549/292

[56] References Cited

U.S. PATENT DOCUMENTS

| | | | |
|---|---|---|---|
| 4,231,938 | 11/1980 | Monaghan et al. | 349/292 |
| 4,293,496 | 10/1981 | Willard | 260/343.5 |
| 4,346,227 | 8/1982 | Terahara et al. | 560/119 |
| 4,444,784 | 4/1984 | Hoffman et al. | 424/279 |
| 4,965,200 | 10/1990 | Chen et al. | 435/125 |

FOREIGN PATENT DOCUMENTS 8613798 4/1979 Japan.
85176595 2/1984 Japan.

OTHER PUBLICATIONS

D. Komagata et al., *J. Antiobiotics*, 39, 1574-1577 (1986).
Conder et al., Discovery and Purification of an Esterase From Clonostachys Compactiuscula Useful for the Biotransformation of Lovastatin Acid to Triol Acid, in Biocatalysis for the 90's Abstract Book, Jun. 5-7, 1991, p. 32.
Enzyme Microb. Technol., 1991, vol. 13, Jun. 1991, p. 526.
Patent Abstracts of Japan, vol. 5, No. 12 (C-40) (684) (1981) Akira Endou and JP-A-55 139 396 (1980).

*Primary Examiner*—Douglas W. Robinson
*Assistant Examiner*—L. Blaine Lankford
*Attorney, Agent, or Firm*—Charles M. Caruso; Melvin Winokur; Catherine A. Dolan

[57] ABSTRACT

Biosynthetic production of 7-[1',2',6',-7',8',8a'(R)-hexahydro-2'(S),6'(R)-dimethyl-8'(S)-hydroxy-1'(S)-naphthyl]-3(R),5(R)-dihydroxyheptanoic acid, "triol acid", is accomplished by enzymatic hydrolysis of lovastatin acid or a salt thereof, by treating it with *Clonostachys compactiuscula* ATCC 38009 or ATCC 74178, or mutants thereof, or a cell-free extract derived therefrom, or a hydrolase derived therefrom. The triol acid and its lactone form are both inhibitors of HMG-CoA reductase and thus useful as anti-hypercholesterolemic agents, and may also serve as intermediates for preparation of other HMG-CoA reductase inhibitors. Also, in the synthesis of simvastatin by direct methylation of lovastatin, selective hydrolysis of residual lovastatin salt by treatment with *Clonostachys compactiuscula* ATCC 38009 or ATCC 74178 or mutants thereof or a cell-free extract derived therefrom, or a hydrolase derived therefrom yields the "triol" salt which can be easily separated from simvastatin.

26 Claims, No Drawings

BIOSYNTHETIC PRODUCTION OF 7-[1',2',6',7',8',8A'(R)-HEXAHYDRO-2'(S),6'(R)-DIMETHYL-8'(S)-HYDROXY-1'(S)-NAPHTHYL]-3(R),5(R)-DIHYDROXYHEPTANOIC ACID (TRIOL ACID)

This application is a continuation-in-part of U.S. Ser. No. 07/788,691 filed Nov. 6, 1991, now abandoned which is a continuation of U.S. Ser. No. 07/597,643, now abandoned filed Oct. 15, 1990.

BRIEF SUMMARY OF THE INVENTION

The present invention relates to biosynthetic production of 7-[1',2',6',7',8',8a'(R)-hexahydro-2'(S),6'(R)-dimethyl-8'(S)-hydroxy-1'(S)-naphthyl]-3(R),5(R)-dihydroxyheptanoic acid "triol acid" by microbiological hydrolysis of lovastatin acid, a fermentation product, using the filamentous fungus, *Clonostachys compactiuscula*, or a hydrolase derived therefrom. This invention also relates to the use of this process in the synthesis of simvastatin from lovastatin to facilitate the separation and isolation of simvastatin from unreacted lovastatin starting material.

The triol acid and its lactone form are old compounds, i.e., ones known in the art, and they are inhibitors of 3-hydroxy-3-methylglutaryl-coenzyme A (HMG-CoA) reductase, an enzyme involved in cholesterol biosynthesis. As inhibitors of that enzyme, they are useful as antihypercholesterolemic agents. They find further usefulness as intermediates for the preparation of other antihypercholesterolemic agents, especially those having various side chains at the 8'-position of the polyhydronaphthyl ring. For example, simvastatin, which has a 2,2-dimethylbutyryloxy side chain at the 8'-position, may be prepared using the lactone form of the triol acid as a starting material, in accordance with known procedures.

The selective conversion of lovastatin salt to the triol salt would be useful in the separation of simvastatin from unreacted lovastatin in the production of simvastatin from lovastatin. Lovastatin acid has a 2-methylbutyryloxy side chain in the 8'-position and is difficult to separate from the newly formed simvastatin acid which has a 2,2-dimethyl-butyryloxy side chain at the 8'-position. Applicants have now found that selective cleavage of the 2-methylbutyryloxy side chain from lovastatin acid salt using the process of this invention employing a hydrolase enzyme from *Clonostachys compactiuscula* (ATCC 38009 or ATCC 74178) to yield the triol salt, results in a more easily separable mixture and greater purity of the simvastatin produced.

The present invention also relates to a substantially pure form of a hydrolase enzyme produced by *Clonostachys compactiuscula* ATCC 38009 or ATCC 74178, and mutants thereof, which is capable of hydrolysing lovastatin acid or a salt thereof to triol acid or a salt thereof in accordance with the process of the present invention.

The present invention further relates to mutant strains of *Clonostachys compactiuscula*, ATCC 38009 or ATCC 74178, which are able to produce a hydrolase capable of hydrolysing lovastatin acid or a salt thereof to triol acid or a salt thereof.

The present invention also relates to a process in which the triol acid produced by treating lovastatin acid or a salt thereof with *Clonostachys compactiuscula* ATCC 38009 and ATCC 74178, or mutants thereof, or a hydrolase derived therefrom, is thereafter converted to its lactone form.

BACKGROUND OF THE INVENTION

The present invention is in the field of inhibitors of HMG-CoA reductase which are useful as antihypercholesterolemic agents. It is now well established that hypercholesterolemia is a significant risk factor in the development of cardiovascular disease, particularly atherosclerosis. Compounds which are able to inhibit the HMG-CoA reductase enzyme interfere with and limit the biosynthesis of cholesterol, and in that way function as antihypercholesterolemic agents. Such compounds, especially the natural fermentation products compactin and mevinolin, are now well known. There is a continuous search, nevertheless, for additional analogs which will give improved antihypercholesterolemic performance. The triol acid produced by enzymatic hydrolysis of lovastatin acid using an enzyme derived from *Clonostachys compactiuscula* in accordance with the biosynthetic process of the present invention provides quantities of a starting material for the preparation and production of such semisynthetic analogs.

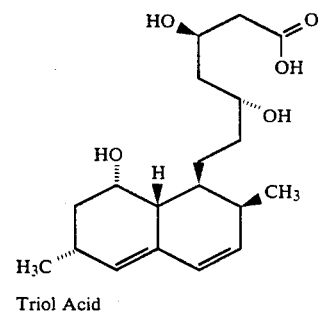

Triol Acid

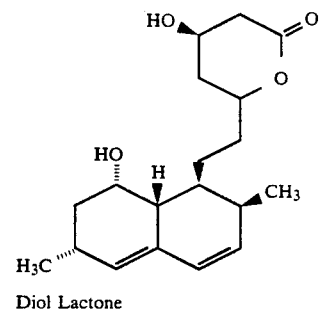

Diol Lactone

The process of this invention may also be conducted starting with pravastatin, which differs from lovastatin in that the 6-α-methyl group on the hexahydronaphthyl ring is replaced with a 6-β-hydroxyl group. Treatment of pravastatin with *Clonostachys compactiuscula* in accordance with the biosynthetic process of the present invention provides the corresponding pravastatin triol acid below.

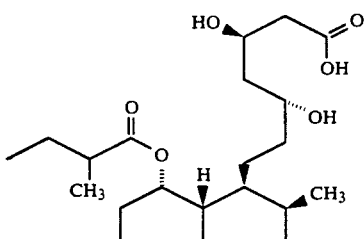

Pravastatin

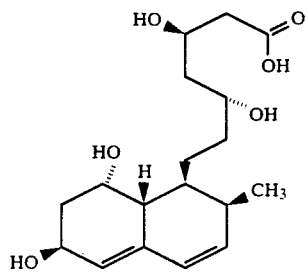

Pravastatin Triol Acid

As already described above, the triol acid and its lactone form are old compounds. The triol acid in its lactone form, for example, is described in Endo, published Japanese Pat. Appln. 86-13798 (1986), where its production by fermentation of *Monascus ruber* and a demonstration of its ability to reduce blood cholesterol levels is also set out. The triol acid in its lactone form, as well as the triol acid itself, are also described in Willard U.S. Pat. No. 4,293,496 (1981). However, in Willard, these compounds are prepared by chemical hydrolysis to remove the 8-(α-methylbutyryloxy) ester side chain of lovastatin, the starting material which is a fermentation product of a particular strain of *Aspergillus terreus*. There is no suggestion that such hydrolysis might be carried out biochemically or microbiologically.

Lovastatin and simvastatin are also compounds known in the art as HMG-CoA reductase inhibitors. The two compounds differ in that lovastatin has a 2-methylbutyryloxy side chain at the 8'-position and simvastatin has a 2,2-dimethylbutyryloxy side chain.

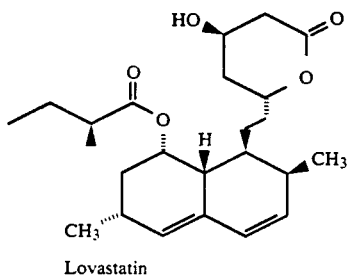

Lovastatin

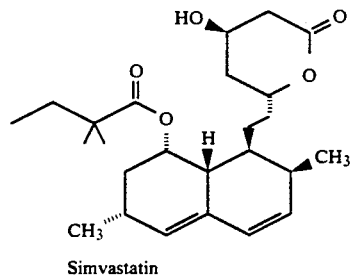

Simvastatin

Although simvastatin has been formed from lovastatin, it has been difficult to separate and purify simvastatin from a mixture of simvastatin and lovastatin. The similarity in structure between the two compounds (the two compounds differ by only one methyl group) makes high pressure liquid chromatography (HPLC) separation difficult because the compounds have such similar retention times. One methodology used to isolate simvastatin from a mixture of simvastatin and lovastatin is to convert the unreacted lovastatin to the triol acid or the diol lactone using base hydrolysis with, for example, sodium hydroxide (NaOH) or lithium hydroxide (LiOH). However, this base hydrolysis hydrolyzes only a percentage of the lovastatin, leaving unreacted lovastatin as a contaminant of the final simvastatin product. An additional problem with the base hydrolysis is partial hydrolysis of the simvastatin, thus reducing the yield of the desired simvastatin product. The present invention provides for a process of isolating simvastatin from mixtures of simvastatin and lovastatin in greater purity and without concomitant yield losses.

Komagata et al., *J. Antibiotics*, 39, 1574–77 (1986), describes enzymatic hydrolytic conversion of compactin (ML-236B) to the 8-hydroxy analog (ML-236A) in which the same side chain is removed as in the present invention. Of 1600 fungal strains investigated, 59 were found to be effective in catalyzing the hydrolytic reaction, and *Emericella unguis* showed the most potent activity. However, *C. compactiuscula* is not disclosed.

Endo, published Japanese Pat. Appln. 85-176595 (1985) describes the same conversion as Komagata et al. above, but additionally includes conversion of "monacolin K" (which is lovastatin) to "monacolin J", (which is the triol acid in the present invention). Especially useful are said to be the molds *Mortierella isabellina, Emericella unguis, Diheterospora chlamydosporia, Humicola fuscoatra, Dichotomomyces cejpii, Neocosmospora africana, Xylogone sphaerospora, Torulomyces ragena,* and *Thielavia fimeti.* However, the highest conversion rate is 78% for a starting material concentration of 0.5 mg/ml, compared to 90–100% with the present invention. And, there is an indication in the related Komagata et al. paper that at higher concentrations, such as the 2.5 mg/ml employed in the present invention, there is a significant drop-off in efficiency of the enzyme. Thus, there is no suggestion in the prior art of the improved microbiological hydrolysis which can be achieved using *Clonostachys compactiuscula.*

Lovastatin can be converted to a more active HMG-CoA reductase inhibitor by C-methylation of the natural 2(S)-methylbutyryloxy side chain to obtain simvastatin. C-methylation may be accomplished by any known process amenable to the functionalities of the molecule.

One process for direct C-methylation of the 2(S)-methylbutyryloxy side chain is described in U.S. Pat. No. 4,582,915. This process is detailed in Scheme I and in the description which follows.

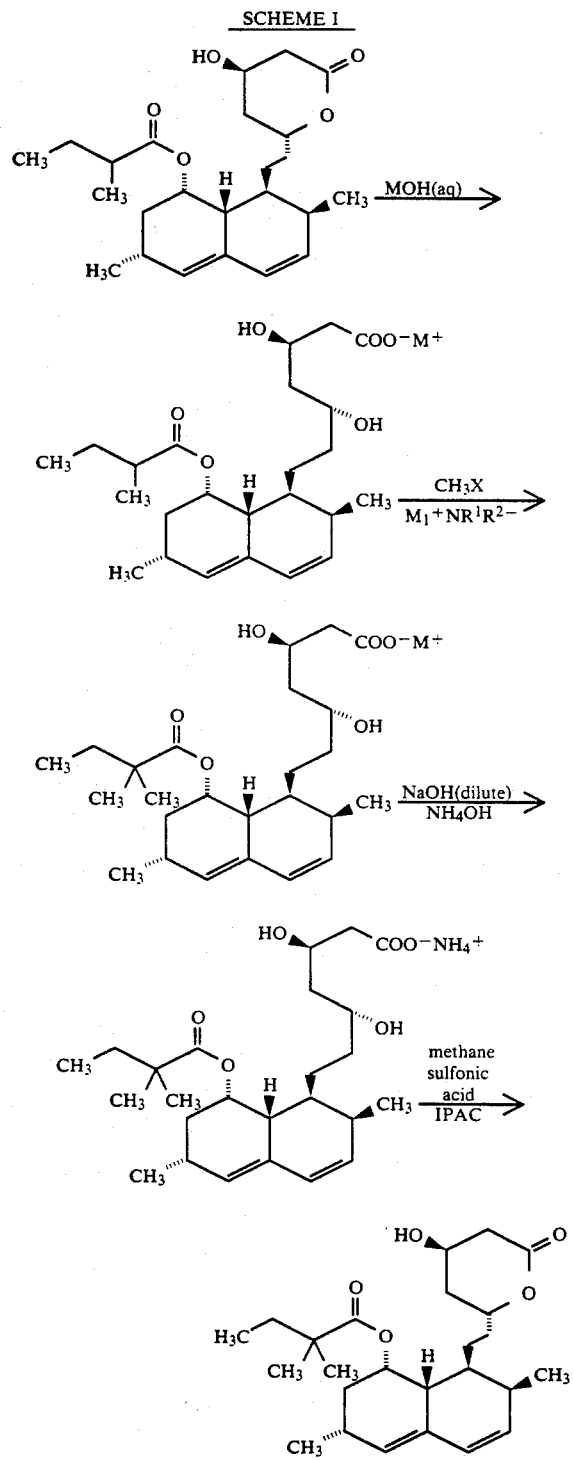

wherein:

M is an alkali metal salt, preferably potassium;

X is halo, such as chloro, bromo or iodo, preferably bromo or iodo;

$M_1^+$ is a cation derived from lithium, sodium or potassium, preferably lithium; and $R^1$ and $R^2$ are 1) independently $C_{1-3}$alkyl, or
2) $R^1$ and $R^2$ joined together form a 5- or 6-membered heterocycle such as pyrrolidine or piperidine with the nitrogen to which they are attached, preferably pyrrolidine.

In the process of forming simvastatin by the direct methylation of lovastatin, the lovastatin lactone compound is first converted to an alkali metal salt, preferably a potassium salt of the dihydroxycarboxylate. Although any conceivable method preparing a dry salt would suffice, it is convenient to add a substantially stoichiometric amount of aqueous potassium hydroxide to a solution of the lactone starting material in a hydrocarbon solvent such as benzene, toluene or cyclohexane containing a small amount of a $C_{1-3}$ alkanol, preferably isopropanol, ethanol or methanol, or alternatively in tetrahydrofuran (THF) with or without added alkanol, stirring for a few minutes to about an hour and finally concentrating to dryness in vacuo. The residue is subjected to rigorous drying such as by azeotropic distillation with cyclohexane, toluene or dry tetrahydrofuran, preferably extremely (less than 0.08 mg $H_2O$/mL) dry tetrahydrofuran.

The dry alkali metal salt is dissolved in an ethereal solvent such as tetrahydrofuran, diethyl ether, 1,2-dimethoxyethane, cooled to about −80° C. to −25° C., preferably −35° C. to −30° C. and treated with an excess of a strong base such as an alkali metal amide, wherein the alkali metal is lithium, sodium or potassium, preferably lithium, and the amide is diethylamide, pyrrolidide, dimethylamide or diisopropyl amide in an ethereal solvent in a dry, inert environment. After about 2 to 8 hours, preferably about two hours at −80° to −25° C., preferably −35° to −30° C., a methyl halide, such as methyl bromide, methyl chloride or methyl iodide, preferably methyl bromide or methyl iodide, is added to the mixture while maintaining the low temperature. Treatment with the strong base and methyl halide as described can be repeated if appreciable amounts of starting material remain. After 0.5 to about 3 hours following final addition of methyl halide, the reaction mixture is quenched by adding to it excess water.

Following this direct methylation, attempts to convert unreacted lovastatin to the triol acid or the diol lactone for final product purification purposes were made using NaOH or LiOH. However, this base hydrolysis hydrolyzed only a small percentage of the lovastatin. Thus, unreacted lovastatin remained as a contaminant of the final simvastatin product. Furthermore, the base hydrolysis also hydrolyzed simvastatin, thus reducing yields of the desired simvastatin product. Following hydrolysis, the open ring acid form of simvastatin or a salt form thereof was then converted to the lactone by either heat or acid-catalyzed lactonization, and separated and purified by crystallization.

DETAILED DESCRIPTION OF THE INVENTION

The present invention is concerned with biosynthetic production of 6(R)-[2-(8(S)-hydroxy-2(S), 6(R)-dimethyl-1′,2′,6′,7′,8′,8a′(R)-hexahydronaphthyl)-ethyl]-4(R)-hydroxy-3,4,5,6-tetrahydro-2H-pyran-2-one, the triol acid (2), or a salt form thereof by treating lovastatin (1) or a salt thereof with *Clonostachys compactiuscula* or mutants thereof, or a cell-free extract derived therefrom, or a hydrolase derived from *Clonostachys compac-*

*tiuscula*. The triol acid may be subsequently converted by known chemistry to its lactone form (3).

The term "mutant" refers to an organism in which some gene (or its regulatory region of DNA) on the genome is modified, leaving the gene or genes responsible for the organism's ability to hydrolyze lovastatin acid to the triol acid functional and heritable. Mutants within the scope of this invention have essentially the same characteristics as those of the parent strain, ATCC 38009.

The starting material for the method of the present invention is lovastatin acid (1), the open-ring form of lovastatin, or a salt thereof. The acid form is the material produced by fermentation of *Aspergillus terreus* in accordance with culturing methods known in the art. Lovastatin itself is too insoluble in aqueous systems to be a useful starting material in the method of the present invention; and those solvents in which it is soluble are generally incompatible with the method of the present invention.

The lovastatin acid starting material will typically be employed in the salt form. Unless otherwise specified, the terms "acid", "open ring acid" and "acid form", when applied to the starting materials, intermediates and final products of the present invention, include any suitable salt form thereof as well. Any salt which permits good solubility and which will not interfere with the other conditions encountered in carrying out the particular reaction is permissible. For example, the alkali metal salts, such as lithium, sodium and potassium; alkaline earth metal salts, such as calcium or magnesium; or salts with other metals such as aluminum, iron, zinc, copper, nickel or cobalt; amino acid salts formed from basic amino acids, such as arginine, lysine, $\alpha,\beta$-diaminobutyric acid and ornithine; amine salts such as t-octylamine, dibenzylamine, ethylenediamine, morpholine, and tris(hydroxymethyl)aminomethane; or the ammonium salt may be employed. The alkali metal salts (Li, Na, and K) and the ammonium salt forms of the lovastatin acid may be employed and are preferred. Especially preferred are the potassium and ammonium salt forms.

For convenience, the structural formulas for lovastatin acid, the triol, acid, and its lactone form, are set out below as Formulas 1, 2, and 3, respectively:

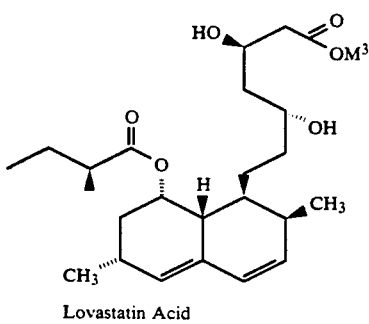

Lovastatin Acid

-continued

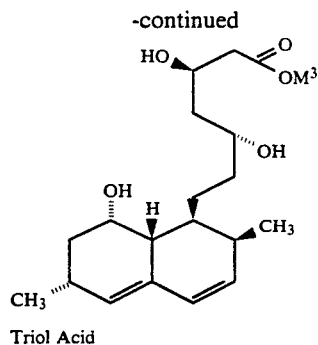

Triol Acid

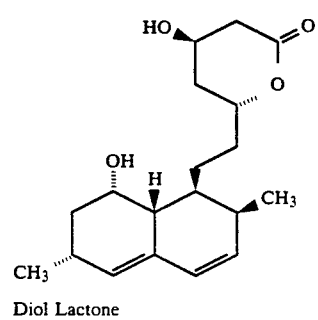

Diol Lactone wherein:

$M^3$ is selected from the group consisting of
a) H,
b) an alkali metal salt such as Li, Na or K,
c) an alkaline earth metal salt such as Ca or Mg,
d) a salt with other metals such as Al, Fe, Zn, Cu, Ni or Co,
e) an amino acid salt formed from a basic amino acid such as arginine, lysine, $\alpha,\beta$-diaminobutyric acid, or ornithine,
f) an amine salt such as t-octylamine, dibenzylamine, ethylenediamine, morpholine, or tris(hydroxymethyl) aminomethane, and
g) the ammonium salt.

The basic mechanism of biosynthetic production of triol acid in accordance with the present invention is though to be enzymatic hydrolysis of lovastatin acid whereby an enzyme produced by *Clonostachys compactiuscula* ATCC 38009 or ATCC 74178, or mutants thereof, catalyzes removal of the 8-($\alpha$-methylbutyryloxy) ester side chain of lovastatin to give the triol acid. As already explained, for reasons of solubility in aqueous systems, it has been found most desirable to use the lovastatin starting material in its open ring or acid form, and for this purpose the ammonium, potassium, sodium and lithium salt forms of lovastatin acid are preferred.

The enzyme produced by *Clonostachys compactiuscula* ATCC 38009 or ATCC 74178 or a mutant thereof may be brought into contact with the lovastatin acid starting material in any number of ways, all of which will be apparent to the person of ordinary skill in this art. All of these are within the definition of the term "treating" as defined in this invention. For example, whole cells may be used, and in accordance with this procedure, a fermentation culture of *Clonostachys compactiuscula* is produced to which the lovastatin acid starting material is simply added and the triol acid final product recovered.

A variation of this whole cell procedure is one in which a fermentation culture of *Clonstachys compactiuscula* as described above is produced, but a small concentration (0.5 to 2.5 g/L, preferably 1.0 to 2.0 g/L) of lovastatin acid is added for the purpose of inducing hydrolytic activity. The cell mass is then harvested by centrifugation or filtration and recovered as pellets or as a hyphal mat which can be used immediately or frozen for later use. These may be added to the lovastatin acid starting material where the latter is present in the fermentation culture in which it has been produced, e.g., by fermentation of *Aspergillus terreus*. Alternatively, the lovastatin acid may be separated from its culture medium and then brought into contact with the frozen pellets of *Clonostachys compactiuscula* described above.

It is not necessary that the whole cells of *Clonostachys compactiuscula* be alive as described above. It is also possible to employ dead cells, e.g., those which have been acetone-dried.

As an alternative to whole cells, it is possible to use crude homogenates derived from these whole cell cultures. It is also possible to isolate the hydrolytic enzyme itself from the crude homogenates and employ the substantially purified enzyme.

The process of bringing the *Clonostachys compactiuscula* enzyme into contact with the lovastatin acid starting material may be carried out batch-wise, or it may be carried out in a continuous manner. The contacting of these reactants themselves may be modified in various ways in keeping with advances in process technology. Thus, an immobilized enzyme column may be employed for the *Clonostachys compactiuscula* enzyme with the lovastatin acid starting material being passed through the column. Another example of such process technology is that relating to membrane reactors. Another alternative process for contacting of the reactants would be to culture the *Clonostachys compactiuscula* ATCC 38009 or ATCC 74178, or mutants, in the same fermentation broth used to produce the lovastatin. It would also be possible to modify that fermentation broth, if necessary, in order to support growth of *Clonostachys compactiuscula* once the lovastatin acid is produced, by adding culture media elements and then introducing the *Clonostachys compactiuscula* ATCC 38009 or ATCC 74178, or mutants thereof, and culturing it to produce the triol acid. This approach, however, is not likely to produce optimum yields. The preferred methods of contacting the reactants is by way of the immobilized enzyme column described above or by using a purified enzyme preparation.

Working examples set out further below describe the method currently employed to demonstrate the enzymatic hydrolysis of lovastatin acid. However, the methods in those working examples would not necessarily be suggestive of methods which would be utilized for commercial production.

The use of the process of this invention to separate and purify simvastatin from mixtures of simvastatin and lovastatin is shown in Scheme II.

The mixture of the simvastatin and lovastatin lactones is converted to a mixture of the corresponding open-ring acids, preferably by treatment with an essentially stoichiometric aqueous alkali hydroxide such as potassium hydroxide or sodium hydroxide in a hydrocarbon solvent such as benzene, toluene or cyclohexane containing a small amount of a $C_{1-3}$ alkanol, preferably isopropanol, ethanol or methanol, stirring for a few minutes to about an hour. The substrate is then extracted into an aqueous medium, such as TRIS (Tris(hydroxymethyl)aminomethane), glycine, TES (N-tris[Hydroxymethyl)methylamino]-2-hydroxy-propane-sulfonic acid), sodium phosphate, MOPSO (3-[N-Morpholino]-2-hydroxypropanesulfonic acid), BIS-TRIS PROPANE (1,3-bis[tris(Hydroxymethyl)-methylamino]propane), BES (N,N-bis[2-hydroxyethyl]-2-aminoethanesulfonic acid), MOPS (3-[N-Morpholino]propanesulfonic acid), HEPES (N-[2-Hydroxyethyl]piperazine-N'-[2-ethanesulfonic acid]), DIPSO (3-[N,N-bis(2-Hydroxyethyl)amino]-2-hydroxypropanesulfonic acid), TAPSO (3-[N-tris(Hydroxymethyl)methylamino]-2-hydroxypropanesulfonic acid), HEPPSO (N-[2-Hydroxyethyl]piperazine-N'-[2-hydroxypropanesulfonic acid]), POPSO (Piperazine-N,N'-bis[2-hydroxypropane sulfonic acid]), EPPS (N-[2-Hydroxyethyl]piperazine-N'-[3-propanesulfonic acid], TEA (N-tris[Hydroxymethyl]methyl-2-aminoethanesulfonic acid), TRICINE (N-tris[Hydroxymethyl]-methylglycine), BICINE (N,N-bis[2-Hydroxyethyl]-glycine), TAPS (N-tris[Hydroxymethyl]methyl-3-aminopropanesulfonic acid), AMPSO (3-[(1,1-Dimethyl-2-hydroxyethyl)amine]2-hydroxypropanesulfonic acid) or CHES (2-[N-Cyclohexylamino]-2-hydroxypropanesulfonic acid) buffers, pH 7–10, 25 mM to 1M; distilled water, or one of the aqueous media listed above supplemented with up to 20% (vol./vol.) of a water-miscible solvent such as methanol, ethanol, propanol, butanol, tetrahydrofuran, or acetone. Preferred are TRIS, glycine, TES and sodium phosphate buffers, pH 7.5–9.5, 25 mM to 75 mM. The dissolved substrate is then treated with *Clonostachys compactiuscula*, (ATCC 38009 or ATCC 74178) or a mutant thereof or a cell-free extract derived therefrom or a hydrolase derived from *Clonostachys compactiuscula* or the substrate is converted to the ammonium salt and treated with *Clonostachys compactiuscula*, or a mutant thereof or a cell-free extract derived therefrom or a hydrolase derived therefrom. The aqueous system may be added prior to or simultaneous with the addition of *Clonostachys compactiuscula*, mutants thereof, or the cell-free extract derived therefrom or the hydrolase derived from *Clonostachys compactiuscula*.

Lactonization by either acid-catalyzed or heat-catalyzed methods, for example, by stirring in isopropylacetate (IPAC) containing 7 mM methane sulfonic acid for two hours at room temperature follows. The resulting simvastatin lactone and diol lactone are separable by high pressure liquid chromatography (HPLC) or by crystallization to obtain substantially pure simvastatin.

Reversed-phase HPLC is conducted using as a mobile phase an organic-aqueous mixture with the aqueous component being 0.01 to 1.0% phosphoric acid or trifluoroacetic acid or other suitable acid and suitable organic components include acetonitrile, methanol and ethanol.

SCHEME II

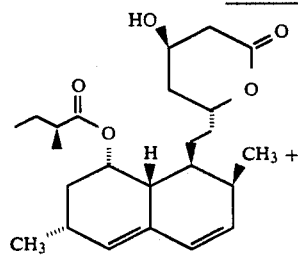

-continued
SCHEME II

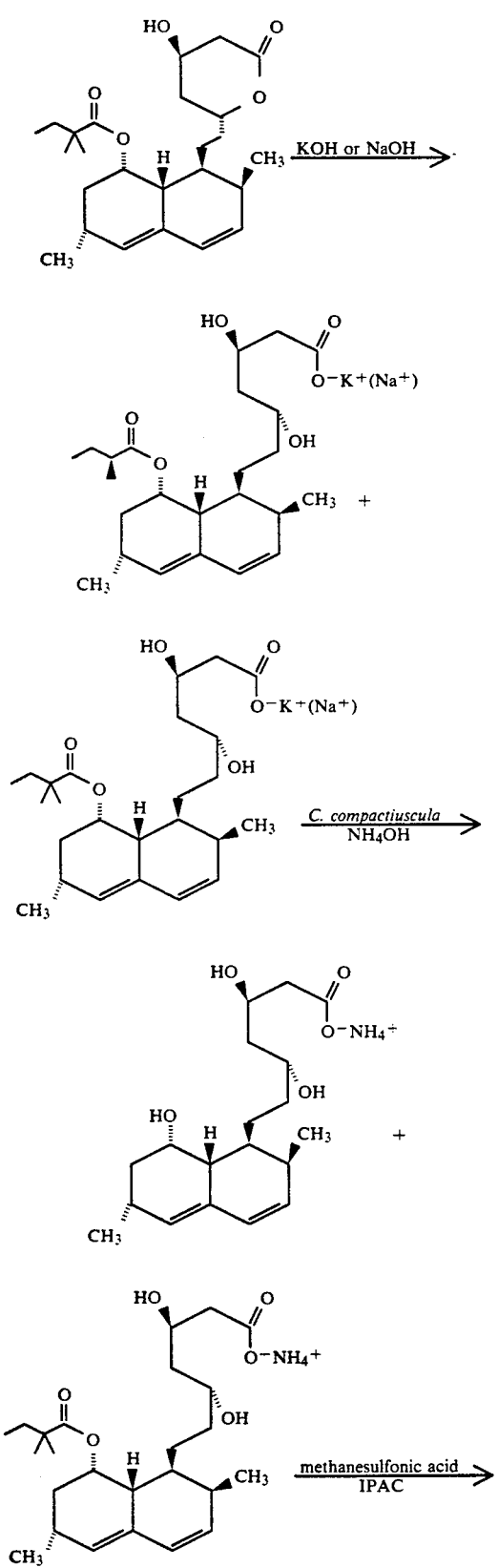

separable by crystallization, HPLC

Simvastatin may also be purified by crystallization from ethyl acetate, isopropyl acetate and methanol.

The enzymatic hydrolysis of lovastatin acid to the triol acid can also be employed in the process for making simvastatin by direct methylation of lovastatin. This overall process is shown in Scheme III.

In the process of forming simvastatin by the direct methylation of lovastatin, the lovastatin lactone compound is first converted to an alkali metal salt, preferably potassium salt of the dihydroxycarboxylate. Although any conceivable method of preparing a dry salt would suffice, it is convenient to add a substantially stoichiometric amount of aqueous potassium hydroxide to a solution of the lactone starting material in a hydrocarbon solvent such as benzene, toluene or cyclohexane containing a small amount of a $C_{1-3}$alkanol, preferably isopropanol, ethanol or methanol, or alternatively employing tetrahydrofuran (THF), with or without the added alkanol, stirring for a few minutes to about an hour and finally concentrating to dryness in vacuo. The residue is subjected to rigorous water removal such as by azeotropic distillation with cyclohexane, toluene, or dry tetrahydrofuran, preferably extremely (less than 0.08 mg H$_2$O/mL) dry tetrahydrofuran.

The dry alkali metal salt is dissolved in an ethereal solvent such as tetrahydrofuran, diethyl ether, 1,2-dimethoxyethane or the like, cooled to about −80° C. to −25° C., preferably −35° C. to −30° C. and treated with an excess of a strong base such as an alkali metal amide, wherein the alkali metal is lithium, sodium or potassium, preferably lithium, and the amide is diethylamide, pyrrolidide, dimethylamide or diisopropyl amide in an etheral solvent in a dry inert environment. After about 2 to 8 hours, preferably about two hours at −80° to −25° C., preferably −35° to −30° C., a methylhalide, such as methyl bromide, methyl chloride or methyl iodide, preferably methyl bromide or methyl iodide, is added to the mixture while maintaining the low temperature. Treatment with the strong base and methyl halide as described can be repeated if appreciable amounts of starting material remain. After 0.5 to about 3 hours following final addition of methyl halide, the reaction mixture is quenched by adding to it excess water.

SCHEME III

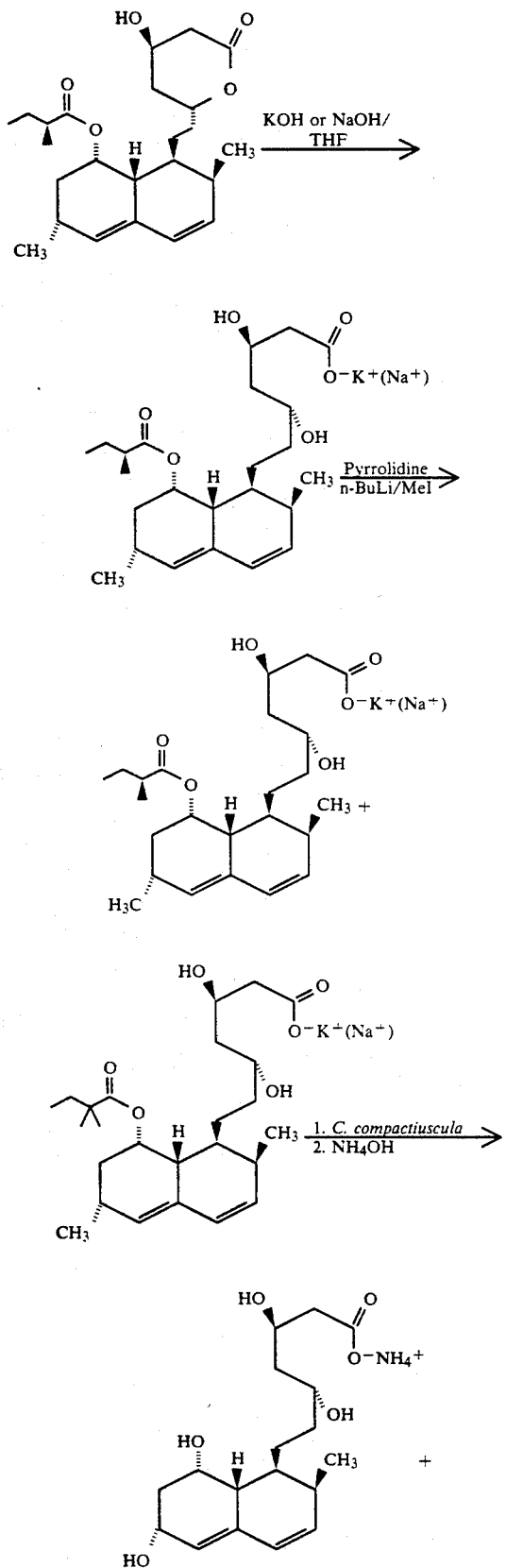

-continued
SCHEME III

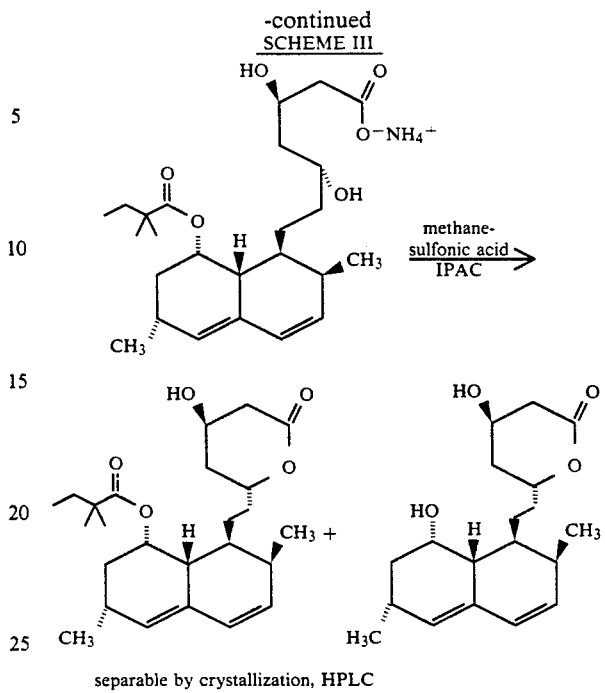

separable by crystallization, HPLC

The mixture of lovastatin acid salt and simvastatin acid salt is then preferably converted to the corresponding ammonium salt by ammonium hydroxide-methanol in ethyl acetate and treating with *Clonostachys compactiuscula*, or a mutant thereof or a hydrolase derived therefrom.

Alternatively the *Clonostachys compactiuscula* enzyme is added directly to the mixture of lovastatin salt and simvastatin salt following the removal of residual organics by distillation.

The resulting mixture of simvastatin acid and triol acid may be converted to the corresponding mixture of lactones by a suitable method, for example, heat-catalyzed or acid-catalyzed lactonization. Simvastatin is separable from the resulting mixture of simvastatin and diol lactone by HPLC or crystallization. Alternatively, the simvastatin acid may be separated from the triol acid by HPLC or crystallization, followed by conversion of the pure simvastatin acid to simvastatin lactone. If the simvastatin acid is to be isolated and purified by crystallization, it is preferred to convert the simvastatin acid to the ammonium salt prior to lactonization.

The present invention is also directed to mutants of the particular strain of *Clonostachys compactiuscula*, ATCC 38009 or ATCC 74178, which are capable of converting lovastatin acid to triol acid. There are techniques well known in the fermentation art for improving the yields of desired products produced by various strains of microorganisms. For example, a given producing strain may be irradiated or exposed to other stimuli known to greatly increase the ongoing mutation of the genetic material of the microorganism. By using a sensitive screen, it is then possible to select from the many mutations thus produced only those which result in an enhanced production of the desired product. In this way, it is usually possible to continually improve the output of a producing strain through its various selected descendants. A biologically pure culture of a mutant is a culture that consists substantially of one strain of the mutant. With regard to the present invention, similar improvements in output of lovastatin acid hydrolase by selected mutants of *Clonostachys compactiuscula* ATCC 38009 or ATCC 74178, may be achieved. A satisfactory screen for this purpose is the use of high performance liquid chromatography (HPLC) which can detect the enzymatic cleavage products at very low concentrations, thus clearly establishing that triol acid has been produced by any particular mutant in question.

Culture Medium

The fermentation of *Clonostachys compactiuscula* is carried out in aqueous media such as those employed for the production of other fermentation products. Such media contain sources of carbon, nitrogen and inorganic salts assimilable by the microorganism.

In general, carbohydrates such as sugars, for example, lactose, glucose, fructose, maltose, mannose, sucrose, xylose, mannitol and the like and starches such as grains, for example, oats, ryes, cornstarch, millet, corn meal and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 1% and 6% by weight of the medium. These carbon sources can be used individually, or several such carbon sources may be combined in the medium. In general many proteinaceous materials may be used as nitrogen sources in the fermentation process. Suitable nitrogen sources include for example, yeast hydrolysates, primary yeast, soybean meal, cottonseed flour, hydrolysates of casein, corn steep liquor, distiller's solubles or tomato paste and the like. The sources of nitrogen either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium. In addition, if necessary, a defoaming agent such as polyethylene glycol or silicone may be added, especially if the culture medium foams seriously.

It should be noted that the media described in the Examples are merely illustrative of the wide variety of media which may be employed, and are not intended to be limitative. Specifically, the carbon sources used in the culture media include dextrose, dextrin, oat flour, oatmeal, molasses, citrate, soybean oil, glycerol, malt extract, cod liver oil, starch, ethanol, figs, sodium ascorbate and lard oil. Included as nitrogen sources were peptonized milk, autolyzed yeast, yeast RNA, tomato paste, casein, primary yeast, peanut meal, distillers solubles, corn steep liquor, soybean meal, corn meal, NZ amine, bean extract, aspargine, cottonseed meal an ammonium sulfate. The major ionic components are $CaCO_3$, $KH_2PO_4$, $MgSO_4.7H_2O$ and NaCl and small amounts of $CoCl_2.6H_2O$ and traces of Fe, Mn, Mo, B, Co and Cu were also present.

Lactonization

Treatment of lovastatin acid with *Clonostachys compactiuscula* ATCC 38009 or ATCC 74178, or mutants thereof, or a cell-free extract derived therefrom, or a hydrolase derived therefrom, in accordance with the process of the present invention provides the triol acid as the predominant product. However, it is also desirable to obtain the lactone form of this compound, since it is also useful as an antihypercholesterolemic agent or as an intermediate for preparing such agents. Lactonization of triol acid is carried out using standard procedures, i.e., either heat or acid catalyzed lactonization. Procedures for acid-catalyzed lactonization of lovastatin acid-related compounds are known and described in U.S. Pat. No. 4,916,239. For simvastatin acid and the triol acid, lactonization has been carried out by stirring in isopropyl acetate containing 7 mM methane sulfonic acid for 2 hours at room temperature.

EXAMPLE 1

Biotransformation of lovastatin acid to triol acid by whole cells of *Clonostachys compactiuscula*

*Clonostachys compactiuscula* ATCC 38009 was grown in a 2L airlift fermentor with 1.8L working volume in medium EN (glucose 1%; peptone 0.2%; beef extract 0.1%; yeast extract 0.1%; and corn steep liquor 0.3%), at 29° C., at an aeration rate of 1.25 vvm, for 48–72 hrs. Lovastatin ammonium salt was added (0.5 g/L final concentration) to induce hydrolytic activity. The fermentation was harvested 24–72 hrs. after addition of the lovastatin ammonium salt by straining through a sieve and washing the pellets with buffer (20 mM Tris, pH 8.5). The cell pellets were frozen until ready to use.

For the biotransformation, *Clonostachys compactiuscula* pellets (17 g wet weight) from an airlift fermentation were contacted with 20 ml of crude lovastatin acid (@20 g/L) in carbonate buffer harvested from an *Aspergillus terreus* fermentation. The biotransformation was carried out in a 250 ml Erlenmeyer flask at 27° C. and 160 rpm. After 17 hrs. approximately 60% of the lovastatin acid was converted to triol acid.

In an additional experiment, *Clonostachys compactiuscula* pellets from an airlift fermentation (5 g wet weight) were contacted with 10 ml crude lovastatin acid (3.5 g/L) extracted from an *A. terreus* fermentation by methanol. The final concentration of methanol in the biotransformation mixture was 25%. The bioreaction was carried out in a 250 ml Erlenmeyer flask at 27° C. and 160 rpm. After 2 hrs. the biotransformation employing *Clonostachys compactiuscula* converted nearly 100% of the lovastatin acid to triol acid, as measured by thin layer chromatography.

EXAMPLE 2

Biotransformation of lovastatin acid to triol acid by crude homogenate of *Clonostachys compactiuscula*.

*Clonostachys compactiuscula* ATCC 38009 was grown in 250 ml shake flasks containing 12 ml of medium EN at 29° C. for 3 days. Lovastatin ammonium salt was added to give a concentration of 2.5 g/L and fermentation was continued for 2 additional days. To prepare the crude homogenate, the culture was harvested by centrifugation at 3000 rpm for 10 minutes, after which it was washed with 50 mM of N-tris(hydroxymethyl)-methyl-2-aminoethanesulfonic acid (TES) buffer, pH 7.7. The culture medium was again centrifuged and the cell mass was chilled on ice and then subjected to grinding in a mortar and pestle containing glass fragments and powdered dry ice. The contents of 1 shake flask was resuspended in 2.0 ml of 50 mM TES buffer and centrifuged at 6000 rpm for 10 minutes to remove cell debris and glass fragments. The supernatant was used as the source of crude homogenate with protein concentration of approximately 0.5 mg/ml.

In order to carry out the biotransformation, one volume of crude homogenate was combined with an equal volume of lovastatin acid ammonium salt (5 g/L), and the mixture was incubated at 29° C. Using this method, 80-90% conversion of lovastatin acid to triol acid was observed within 2 hrs.

EXAMPLE 3

Purification of the lovastatin hydrolyzing enzyme from *C. compactiuscula* cells A hydrolytic enzyme which carries out the biotransformation of lovastatin acid to triol acid was purified by Fast Protein Liquid Chromatography (FPLC*) employing a MONO Q ® anion exchange column to near homogeneity from homogenates of *Clonostachys compactiuscula* employing the procedures described below.

The supernatant from the 6,000 rpm centrifugation as in Example 2 above, but where 50 mM of tris(hydroxymethyl)aminomethane (TRIS) buffer (pH 7.8) is substituted for 50 mM TES buffer, was centrifuged at 15,000 rpm for 20 minutes and the resulting supernatant filtered through a 0.45 mm filter. Batches (10 mL) of filtrate containing 0.3-0.5 mg/mL protein were then applied at a rate of 1.0-2.0 mL/minute to a Pharmacia MONO Q ® (HR 5/5) anion exchange column connected to a Pharmacia Fast Protein Liquid Chromatography (FPLC) system.

After allowing binding of the anionic proteins to the column matrix, the hydrolase was specifically eluted by the application of a linear gradient of sodium chloride (0-500 mM) in 20 mM TRIS, pH 7.8. Eluted protein was collected in 1 mL fractions and assayed either using lovastatin ammonium salt (in which case percent hydrolysis was estimated by TLC (thin-layer chromatography) and densitometry or HPLC), or a colorimetric substrate (ortho-nitrophenyl butyrate, o-NPB) towards which the enzyme had been shown to have hydrolytic activity. When the latter substrate was used, the hydrolytic reaction was monitored spectrophotometrically at 410 nm essentially as described by Lawrence, R. C. et al. in J. Gen. Microbiol. (1967) 48, 401-418. Both assay methods revealed that the hydrolase was eluted when the NaCl concentration approached 300 mM.

Sodium dodecyl sulfate-polyacrylamide (SDS) gel electrophoresis revealed the peak lovastatin acid hydrolase-containing fractions to contain a prominent band of molecular weight approximately 45,000 Da.

Using the purified enzyme preparation, the biotransformation was carried out in accordance with the procedures described above in Examples 1, 2, 4 and 6, and an estimate was made of the hydrolase's Km and specific activity with lovastatin ammonium salt as substrate. The value for Km obtained was 4.14 mM and under saturating substrate conditions the enzyme was found to have a specific activity of 0.04 mmol lovastatin ammonium salt hydrolyzed/mg protein per minute.

EXAMPLE 4

Biotransformation of lovastatin acid to triol acid by purified hydrolase from *Clonostachys compactiuscula*

A hydrolytic enzyme which carries out the biotransformation of lovastatin acid to triol acid was purified by Fast Protein Liquid Chromatography (FPLC*) employing a MONO Q ® anion exchange column to near homogeneity from homogenates of *Clonostachys compactiuscula* employing the procedures described below.

A supernatant from the 6,000 rpm centrifugation as in Example 2 above, but where 20 mM of tris(hydroxymethyl)aminomethane (TRIS) buffer is substituted for 50 mM TES buffer, was centrifuged at 15,000 rpm and the resulting supernatant filtered through a 0.45 micrometer filter. Batches (10 ml) of filtrate containing 0.3-0.5 mg/ml protein were then applied to a Pharmacia MONO Q ® anion exchange column connected to a Pharmacia Fast Protein Liquid Chromatography (FPLC) system.

After allowing binding of the anionic proteins to the column matrix, the hydrolase was specifically eluted by the application of a linear gradient of sodium chloride (0-500 mM). Eluted protein was collected in 1 ml fractions and assayed either using lovastatin ammonium salt (in which case percent hydrolysis was estimated by TLC and densitometry or HPLC), or a colorimetric substrate (ortho-nitrophenyl butyrate o-NPB) towards which the enzyme had been shown to have hydrolytic activity. When the latter substrate was used, the hydrolytic reaction was monitored spectrophotometrically at 410 nm essentially as described by Lawrence, R. C. et al. in J. Gen. Microbiol. (1967) 48, 401-418. Both assay methods revealed that the hydrolase was eluted when the NaCl concentration approached 300 mM.

Sodium dodecyl sulfate-polyacrylamide (SDS) gel electrophoresis revealed the peak lovastatin acid hydrolase-containing fractions to contain a prominant band of molecular weight approximately 45,000 Da.

Using the purified enzyme preparation, the biotransformation was carried out in accordance with the procedures described above in Examples 1 and 2, and an estimate was made of the hydrolase's Km and specific activity with lovastatin ammonium salt as substrate. The value for Km obtained was 4.14 mM and under saturating substrate conditions the enzyme was found to have a specific activity of 0.11 mmol lovastatin ammonium salt/mg protein per hour.

EXAMPLE 5

Biotransformation of lovastatin ammonium salt in the presence of excess simvastatin ammonium salt Forty-five grams of frozen *Clonostachys compactiuscula* (ATCC 38009) cells, which had been grown in medium EN as detailed in Example 5 (and washed with 50 mM Tris buffer, pH 7.8, prior to freezing) was homogenized with glass fragments and dry ice using a mortar and pestle. The resulting homogenized, frozen powder was transferred to a suitable tube and the material remaining in the mortar washed into the same tube using a minimal volume of 50 mM Tris, pH 7.8. The mixture was then allowed to thaw and then centrifuged at 6000 rpm for 10 minutes to remove large cell debris and glass.

The 6000 rpm supernatant was used as a crude source of hydrolase and 0.8 mL was mixed with 0.2 mL methanol and 1.0 mL of a solution of simvastatin (18.6 mM and lovastatin (1.4 mM) ammonium salts in 50 MM Tris, pH 7.8.) The reaction mixture was incubated at 29 C. and sampled after 1 h, 2 h, and 17 h by removing 0.1 mL and diluting with 0.9 mL methanol. The samples were then subjected to analysis by HPLC using a Whatman C-8 column as stationary phase and a 60:40 mixture of acetonitrile: 0.5% phosphoric acid as mobile phase; under these conditions the respective retention times for simvastatin, lovastatin and triol ammonium salts are 4.4 min., 3.8 min., and 2.5 min. After 17 h the area percent of the lovastatin peak had been reduced from 23.2% to 0.7%, representing a greater than 99% conversion. Greater than 96% of the initial simvastatin ammonium salt remained intact over this same contact period.

EXAMPLE 6

Biotransformation of residual lovastatin acid to triol acid following the synthesis of simvastatin acid from lovastatin acid by direct methylation.

Step 1: Preparation of Lovastatin Potassium Salt

A solution of lovastatin (99% pure; 25 g; 60.57 mmol) in 325 mL tetrahydrofuran (THF) was prepared under nitrogen then cooled to 5° C. An aqueous solution (6.1 ml) of 10.01M potassium hydroxide was added over 15 min then the mixture was warmed to 25° C. and aged, with stirring, until complete (>99%) conversion to the potassium salt (by HPLC analysis) had occurred.

Step 2: Preparation of Simvastatin Potassium Salt

The lovastatin potassium salt solution prepared in Step 1 was heated to reflux, distilling a total of 500-700 mL THF through a 10 in. Vigreaux column while maintaining a minimum pot volume of 215 mL with sieve-dried THF. The water content of the lovastatin potassium salt solution was thus reduced to a level of <0.1 mg/mL. This solution was then diluted with 150 mL of sieve-dried THF (water content <0.1 mg water/mL) to give a total volume of 365 mL. Sieve-dried pyrrolidine (5.81 g; 81.7 mmol; water content <0.2 mg/ml) was added as a single batch and the reaction cooled in a dry ice/acetone bath to −78° C. Next, 117 mL of 1.6M n-butyllithium in hexane was added over a one hour period, sub-surface, while maintaining rapid agitation and an internal temperature below −70° C.

The lovastatin potassium salt solution, now containing the lithium pyrrolidide intermediate, was warmed to −35° C. using a dry ice-acetonitrile bath and aged for 2 hours. After recooling to −45° C., 13.32 g of sieve-dried methyl iodide (93.0 mmol; density 2.89 g/mL) was added in one portion and the mixture aged at −30° C. (internal temperature following methyl iodide addition) for 30 minutes. The mixture was quenched with 200 mL water and the phases allowed to separate in a separating funnel. The lower, aqueous, layer was diluted to a volume of 1250 mL by the further addition of water and then cooled to below 10° C. The pH was adjusted to 6 using 6M hydrochloric acid then 250 mL ethyl acetate was added and the pH further adjusted to 2.0 (again using HCl). Phase separation was again allowed to occur then the aqueous layer was re-extracted with 175 mL cold (5°-10° C.) ethyl acetate. The two organic (ethyl acetate) layers were pooled and then washed with 150 mL water before drying the final organic layer over sodium sulfate (to <10 mg/ml water) and filtering. Next, 112.3 mL methanol was charged into the (425 mL) dry, filtered mixture at 25° C. and then 1.3 mL of a methanol:aqueous ammonium hydroxide (3:1) solution was added over a 5 minute period. The mixture was seeded with simvastatin ammonium salt (SAS) and aged for 10 minutes then a further 35.9 mL of the methanol:aqueous ammonium hydroxide (3:1) solution was added dropwise over 1 hour. The mixture was then cooled to −10° C. over 2.5 hours and aged for an additional 1 hour. The product was filtered and washed with 25 mL cold (0° C.) methanol and the resulting white crystals were dried in vacuo to give simvastatin ammonium salt as white needles (87% pure SAS containing 10% residual lovastatin as the ammonium salt).

Step 3: Biotransformation of residual lovastatin acid (as the ammonium salt) to triol acid

*Clonostachys compactiuscula* esterase was purified from 57 g mycelial cells which had been grown up in medium EN using the methods detailed in Examples 1 and 3. The use of a Pharmacia HR 10/10 MONO Q ® column allowed the application of 85 mL of crude cell-free extract per purification run. In total 0.89 mg of purified esterase was obtained (in a volume of 10 mL) which was then concentrated to 0.175 mg protein/mL by ultrafiltration using a 10,000 molecular weight cutoff CENTRIPREP ® device (AMICON ®).

Samples of the esterase were then incubated with the simvastatin ammonium salt prepared by direct methylation of lovastatin; final concentrations of protein were 0.4, 4.0 and 40 microgram/mL and simvastatin concentrations used were 10, 35 and 50 mM. Other conditions which were varied were pH (7.8 and 9.5 were assessed) and methanol concentration (0, 10 and 20% [v/v, final concentration]). The reactions were buffered by the inclusion of either 100 mM TRIS (in the case of reactions carried out at pH 7.8) or 100 mM glycine (pH 9.0). Greater than 90% hydrolysis of residual lovastatin acid to triol acid was obtained within 16 h under the following conditions:

| Enzyme conc. (microgram/ml) | Simvastatin conc. (mM) | pH | Methanol conc. (% v/v) |
|---|---|---|---|
| 4.0 | 10 | 7.8 | 0 |
| 4.0 | 10 | 7.8 | 10 |
| 4.0 | 10 | 9.5 | 0 |
| 4.0 | 10 | 9.5 | 10 |
| 4.0 | 10 | 9.5 | 20 |
| 4.0 | 35 | 9.5 | 10 |
| 40.0 | 35 | 7.8 | 0 |
| 40.0 | 35 | 7.8 | 10 |
| 40.0 | 35 | 9.5 | 0 |
| 40.0 | 35 | 9.5 | 10 |
| 40.0 | 35 | 9.5 | 20 |

EXAMPLE 7

Biotransformation of residual lovastatin acid to triol acid following the synthesis of simvastatin acid from lovastatin acid by direct methylation.

Step 1: Preparation of Simvastatin Ammonium Salt

Starting with 5 g lovastatin, the potassium salt solution in THF is prepared according to Example 6, Step 1. A solution of sieve-dried pyrrolidine (2.48 mL; 2.4 equivalents; 29.67 mmoL; <0.2 mg water/ml) in 12.3 mL sieve-dried THF) is cooled to −20° C. in a dry ice/acetonitrile bath. Then a solution of 1.6M butyllithium in hexane (18.2 mL; 2.35 equivalents) is added at such a rate as to keep the temperature below −10° C. After the addition is complete the lithium pyrrolidide/THF solution is aged at −20° C. for 15 minutes. The dry solution of lovastatin potassium salt in THF is cooled to −35° C. in a dry ice/acetonitrile cooling bath. The lithium pyrrolidide/THF solution at −20° C. is added to the rapidly agitated mixture at such a rate as to maintain the internal temperature below −30° C. at all times throughout the addition. The mixture is aged at −35° C. for 2 hours then, following cooling to −40° C., 1.16 ml (18.67 mmol; 1.5 equivalents) methyl iodide is added to the solution in a single batch which causes the internal temperature of the mixture to rise (to approximately −20° C.); the internal temperature is brought back to $-30°$ C. and aged for 1 hour, then warmed to $-10°$ C. and aged for 30 minutes.

The mixture is quenched with 40 mL water and the phases allowed to separate in a separating funnel. The lower, aqueous, layer is diluted to a volume of 250 mL by the further addition of water and then is cooled to below 10° C. The pH is adjusted to 6 using 6M aqueous hydrochloric acid then 50 mL ethyl acetate is added and the pH further adjusted to 2.0 (again using HCl). Phase separation is again allowed to occur then the aqueous layer was re-extracted with 35 mL cold (5°–10° C.) ethyl acetate. The two organic (ethyl acetate) layers are pooled and then washed with 30 mL water before drying the final organic layer over sodium sulfate and filtering. Next, 22.5 mL methanol is charged into the dry, filtered mixture at 25° C. and then 0.26 mL of a methanol:aqueous ammonium hydroxide (3:1) solution is added over 5 minutes. The mixture is seeded with simvastatin ammonium salt and aged for 10 minutes then a further 7.2 mL of the methanol/ammonium hydroxide is added dropwise over 1 hour. The mixture is then cooled to $-10°$ C. over 2.5 hours and aged for an additional 1 hour. The product is filtered and washed with 5 mL cold (0° C.) methanol and the resulting white crystals are dried in vacuo to give simvastatin ammonium salt.

Step 2: Biotransformation of residual lovastatin acid (as the ammonium salt) to triol acid Biotransformation is conducted according to the procedures in Example 6, Step 3.

EXAMPLE 8

Lactonization of Simvastatin Ammonium Salt and Crystallization and Isolation of Pure Simvastatin Lactone Step 1: Lactonization of Simvastatin Ammonium Salt Distilled water (20 mL) glacial acetic acid (40 mL) and butylated hydroxyanisole (BHA, 50 mg) were charged to a 250 ML 3-neck round bottom flask under a nitrogen atmosphere. The batch temperature was adjusted to 20°–25° C. and simvastatin ammonium salt (12.5 g, 27.56 mmoles) was added and agitated at 20°–25° C. for 15 min. or until dissolved. Methane sulfonic acid (70%, 4.35 g, 30.8 mmoles, 1.118 equiv) was added and the mixture was aged at 20°–25° C. for 2 hours until the lactonization reaction was more than 75% complete.

Percent conversion was determined by HPLC following the conditions in Preparation A. Percent conversion was calculated as follows:

$$\frac{\text{area \% (Simvastatin Ammonium Salt)}}{\text{area \% (Simvastatin Ammonium Salt + Simvastatin)}} \times 100\%$$

Step 2: Crystallization and Isolation of Pure Simvastatin

The batch was seeded with crude Simvastatin seed crystals (60 mg) and aged at 20°–25° C. for 0.5 hour. Distilled water (22.5 mL) was added over 3 hours (0.13 mL/min.) and a second distilled water charge (35 mL was added over one hour (0.58 mL/min.). The batch was aged at 20°–25° C. for one hour and then treated dropwise with 28 w/w % ammonium hydroxide (4.0 mL).

The batch was aged at 20°–25° C. for one hour and filtered to collect the Simvastatin crude crystals. The Simvastatin crude wet cake was washed with 2:1) distilled water:acetic acid (50 mL), distilled water (50 mL) and 1:1 methanol:distilled water (50 mL). The product was dried overnight in vacuo with a nitrogen purge at 25°–30° C. to give the Simvastatin crude as white needles (10.38 g HPLC assay 98 w/w %).

EXAMPLE 9

Crystallization and Isolation of Pure Simvastatin

Crude Simvastatin (10 g, 23.89 mmoles) and butylated hydroxyanisole (50 mg) were charged to a flask containing 126.4 mL degassed methanol under a nitrogen atmosphere. The batch temperature was adjusted to 20°–25° C. and agitated for 15 minutes until solids dissolved. The solution was filtered through a bed of activated carbon, such as ECOSORB C ® which is composed of: water, activated carbon, cellulose fiber, styrene divinyl benzene and anion exchange resin (91.5 g of methanol (50 mL) washed ECOSORB C ®) and the carbon cake is washed with 40 mL of degassed methanol. The combined methanol solution was transferred to a 250 mL 3 neck round bottom flask and heated to 38°–40° C. under a nitrogen atmosphere. Degassed distilled water (83.3 mL) was added subsurface over 30 minutes (2.78 mL/min.) and aged at 38°–40° C. for 30 minutes. The batch was cooled to 25° C. over 1 hour. Degassed distilled water (83.3 mL was charged subsurface over 1 h (1.38 mL/min.) at 25° C. and cooled to 10°–15° C. over 1 hour.

The slurry was filtered and the wet cake was washed with 50 mL of 50% methanol/distilled water (vol./vol.) at 10° C. The product was dried overnight in vacuo with a nitrogen purge at 35°–40° C. to give pure simvastatin as white needles (9.49 g HPLC assay=99 w/w %).

PREPARATION A

HPLC Weight Percent Assay for Dry Simvastatin Crude 30 mg of standard or sample were accurately weighed into a 100 mL volumetric flask and were diluted to the mark with 60:40 acetonitrile: 0.01M $KH_2PO_4$ (pH=4.0).

Column: PERKIN-ELMER ® $C_{18}$, 3 cm length, 3 micron particle size, reversed-phase column
Temperature: 25° C.
Flow rate: 3.0 mL/min
Detection: uv 238 nm
Injection: 5 microliters
Mobile phase: 50:50 acetonitrile: 0.1% $H_3PO_4$ (aq)

| Retention Time: Time (min) | Identity |
|---|---|
| 1.80 | 1. Simvastatin ammonium salt |
| 2.20 | 2. Lovastatin and epimer |
| 3.44 | 3. Simvastatin crude |

The weight % is calculated as follows:

$$\frac{\text{(average response factor of samples) (100)}}{\text{(average response factor of standard)}} = \text{WEIGHT \%}$$

What is claimed is:
1. A process for preparing a compound of Formula 2 in recoverable amounts thereof,

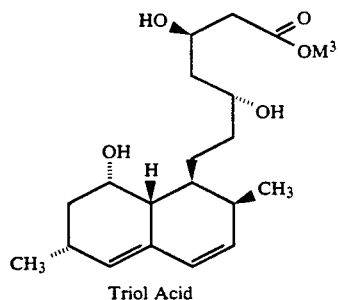

Triol Acid comprising treating a compound of Formula 1

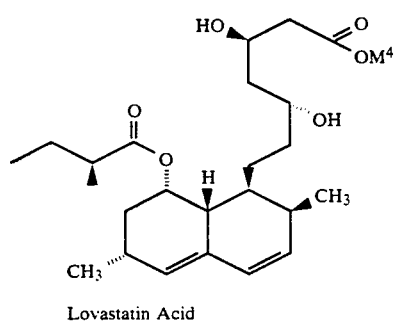

Lovastatin Acid with *Clonostachys compactiuscula* ATCC 38009 or ATCC 74178, or mutants thereof capable of carrying out the process or a cell-free extract derived therefrom, or a hydrolase derived therefrom, and recovering the product wherein:

$M^3$ and $M^4$ are independently:
- a) H,
- b) Li, Na or K,
- c) Ca or Mg,
- d) Al, Fe, Zn, Cu, Ni, or Co,
- e) arginine, lysine, $\alpha,\beta$-diaminobutyric acid, or ornithine,
- f) t-octylamine, dibenzylamine, ethylenediamine, morpholine, or tris(hydroxy-methyl)aminomethane, or
- g) $NH_4$.

2. The process according to claim 1 wherein $M^3$ and $M^4$ are independently:
- a) Li,
- b) Na,
- c) K, or
- d) $NH_4$.

3. The process according to claim 2 wherein $M^3$ is K or $NH_4$.

4. A process for preparing a compound of Formula 7 in recoverable amounts thereof

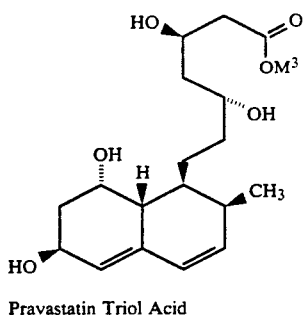

Pravastatin Triol Acid comprising treating a compound of Formula 8 according to the procedures in claim 1.

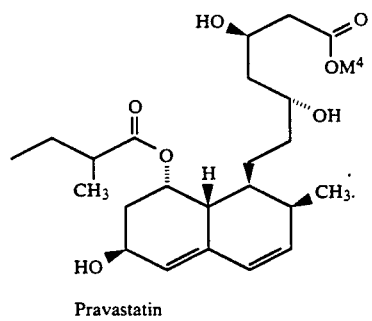

Pravastatin

5. The process according to claim 1 wherein the hydrolase is in a purified form and immobilized on a column, and the compound of Formula 1 is brought into contact therewith by passage through said column.

6. A substantially pure form of the hydrolase enzyme produced by *Clonostachys compactiuscula* ATCC 38009 or ATCC 74178 and mutants thereof, which is capable of carrying out a process according to claim 1.

7. A substantially pure form of an enzyme capable of hydrolyzing Lovastatin Acid to Triol Acid and characterized by:
- a) a molecular weight of approximately 45,000 Daltons;
- b) a $K_m$ with lovastatin ammonium salt substrate of 4.14 mM;
- c) a specific activity, under saturating substrate conditions of 0.04 mmol lovastatin ammonium salt hydrolyzed/mg protein per minute; and
- d) a specific elution on a sodium chloride gradient in 20 mM TRIS pH 7.8 of 300 mM.

8. The process of claim 1 further comprising lactonization of the triol acid or salt thereof of Formula 2 to provide a diol lactone of structural Formula 3:

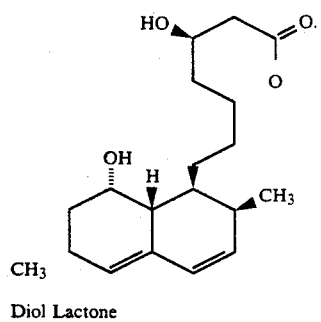

Diol Lactone

9. A process of separating a compound of Formula 4

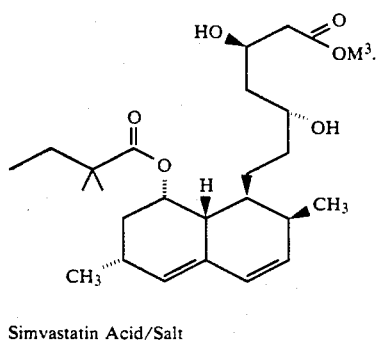

Simvastatin Acid/Salt from a mixture thereof with a contaminant of Formula 1

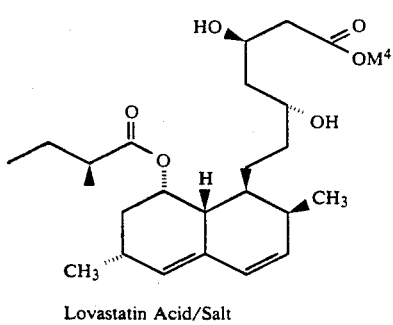

Lovastatin Acid/Salt comprising treating the mixture of the compounds with *Clonostachys compactiuscula* ATCC 38009 or ATCC 74178 or mutants thereof capable of carrying out the process or a hydrolase derived therefrom to convert the compound of Formula 1 to the compound of Formula 2,

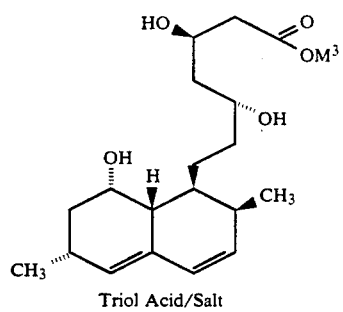

Triol Acid/Salt and separating and isolating the compounds of Formula 4 and Formula 2 in the open acid, salt or lactone form, wherein:

$M^3$ and $M^4$ are independently.
a) H,
b) Na or K,
c) Ca or Mg,
d) Al, Fe, Zn, Cu, Ni, or CO,
e) arginine, lysine, $\alpha,\beta$-diaminobutyric acid, or ornithine,
f) t-octylamine, dibenzylamine, ethylenediamine, morpholine, or tris(hydroxy-methyl)aminomethane, or
g) $NH_4$.

10. The process of claim 9 wherein the separation and isolation of the compounds of Formulae 2 and 4 comprise:

(a) treating with isopropyl acetate and methanesulfonic acid to form the lactones of Formulae 3 and 5:

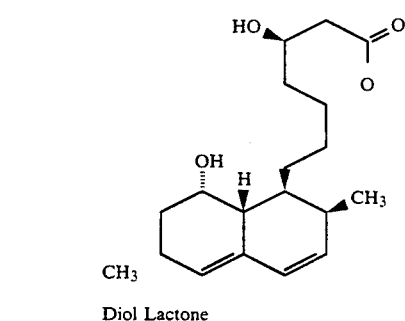

Diol Lactone

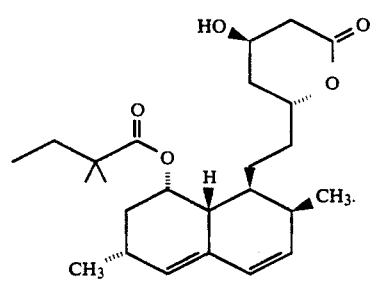

Simvastatin (b) separating and purifying of the compounds of Formulae 3 and 5 by HPLC or crystallization, and
(c) recovering the products in the closed-ring lactone form of Formulae 3 and 5.

11. A process for the preparation of a compound of Formula 4

Simvastatin Acid/Salt (Formula 4)

in recoverable amounts thereof comprising direct methylation of a compound of Formula 1

Lovastatin Acid (Formula 1)

wherein $M^3$ and $M^4$ are as in claim 1, followed by treatment with *Clonostachys compactiuscula* ATCC 38009 or ATCC 74178, or mutants thereof capable of carrying out the process or a hydrolase derived therefrom, and separation by HPLC or crystallization and recovery of the product.

12. The process of claim 11 wherein direct methylation of the compound of Formula 1 or a salt thereof comprises treatment with $CH_3X$ and $M_1{}^+NR^1R^2{}^-$, wherein:

X is:
 a) chloro,
 b) bromo, or
 c) iodo;

$M_1{}^+$ is:
 a) $Li^+$,
 b) $Na^+$, or
 c) $K^+$; or $R^1$ and $R^2$ are
 a) independently $C_{1-3}$alkyl, or
 b) $R^1$ and $R^2$ joined together form a 5 or 6 membered heterocycle such as pyrrolidine or piperidine with the nitrogen to which they are attached.

13. The process of claim 12 wherein $M^3$ is the ammonium salt and $M^4$ is the potassium or ammonium salt.

14. The process of claim 13 wherein the product of Formula 4 is isolated and purified by crystallization.

15. The process of claim 14 wherein the isolated and purified compound of Formula 4 is lactonized to the compound of Formula 5.

16. A process for preparing a compound of Formula 5

Simvastatin (Formula 5)

or a salt thereof in recoverable amounts thereof comprising direct methylation of a compound of Formula 6

Lovastatin (Formula 6)

by conversion of the lactone of Formula 6 to the open ring acid and treatment with $CH_3X$ and $M_1{}^+NR^1R^2{}^-$ wherein:

X is:
 a) chloro,
 b) bromo, or
 c) iodo;

$M_1{}^+$ is:
 a) $Li^+$,
 b) $Na^+$, or
 c) $K^+$; or $R^1$ and $R^2$ are
 a) independently $C_{1-3}$alkyl, or
 b) $R^1$ and $R^2$ joined together form a 5 or 6 membered heterocycle such as pyrrolidine or piperidine with the nitrogen to which they are attached;

followed by treatment with *Clonostachys compactiuscula* ATCC 38009 or ATCC 74178, mutants thereof capable of carrying out the process or a hydrolase derived therefrom, lactonization, and separation by HPLC or crystallization and recovery of the product.

17. The process of claim 9 wherein the products are separated by crystallization.

18. The process of claim 10 wherein the products are separated by HPLC.

19. The process of claim 16 wherein the product is purified by HPLC.

20. The process of claim 9 wherein the compound of Formula 4 and the compound of Formula 1 are present as the ammonium salt form.

21. The process of claim 9 wherein the mixture is treated with a purified form of the hydrolase of *Clonostachys compactiuscula*.

22. The process of claim 10 wherein the mixture is treated with a purified form of the hydrolase of *Clonostachys compactiuscula* ATCC 38009 or ATCC 74178.

23. The process of claim 16 wherein the mixture is treated with a purified form of the hydrolase of *Clonostachys compactiuscula* ATCC 38009 or ATCC 74178.

24. The process of claim 19 wherein the mixture is treated with a purified form of the hydrolase of *Clonostachys compactiuscula* ATCC 38009 or ATCC 74178.

25. The process of claim 15 wherein lactonization is accomplished by treatment with isopropylacetate and methanesulfonic acid.

26. The process of claim 25 wherein X is iodo, and $R^1R^2$ are joined together and form pyrrolidine with the nitrogen to which they are attached.

* * * * *